United States Patent
Ohkawa et al.

(10) Patent No.: US 6,368,769 B1
(45) Date of Patent: Apr. 9, 2002

(54) AROMATIC SULFONIUM COMPOUNDS, PHOTOACID GENERATORS COMPRISING THE SAME, PHOTOPOLYMERIZABLE COMPOSITIONS CONTAINING THE SAME, STEREOLITHOGRAPHIC RESIN COMPOSITIONS, AND STEREOLITHOGRAPHIC PROCESS

(75) Inventors: Kazuo Ohkawa; Hiroyuki Tachikawa; Satoyuki Chikaoka, all of Tokyo (JP)

(73) Assignee: Asahi Denki Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/555,632
(22) PCT Filed: Dec. 4, 1998
(86) PCT No.: PCT/JP98/05472
§ 371 Date: Jul. 6, 2000
§ 102(e) Date: Jul. 6, 2000
(87) PCT Pub. No.: WO99/28295
PCT Pub. Date: Jun. 10, 1999

(30) Foreign Application Priority Data

Dec. 4, 1997 (JP) ............................................... 9-334529
Oct. 14, 1998 (JP) ........................................... 10-291898

(51) Int. Cl.[7] .......................... G03F 7/004; C08F 59/40; C08F 2/50; C08F 20/20; C07C 381/12
(52) U.S. Cl. ................................ 430/270.1; 430/280.1; 430/288.1; 430/269; 568/42; 568/43; 522/15; 522/25; 522/31; 522/2; 264/401
(58) Field of Search ....................... 568/42, 43; 522/15, 522/25, 31, 2; 562/499, 806; 430/280.1, 270.1, 288.1, 269; 264/401

(56) References Cited

U.S. PATENT DOCUMENTS 5,985,510 A * 11/1999 Akutsu et al. .............. 430/269

FOREIGN PATENT DOCUMENTS

| JP | A761964 | 3/1995 |
| JP | A10226658 | 8/1998 |

OTHER PUBLICATIONS

Patent Abstracts of Japan 10226658A, Aug. 25, 1998.
Patent Abstracts of Japan 07061964A, Mar. 7, 1995.

* cited by examiner

Primary Examiner—Cynthia Hamilton
(74) Attorney, Agent, or Firm—Birch, Stewart, Kolasch & Birch, LLP

(57) ABSTRACT

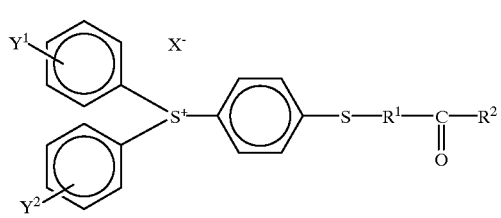

(1)

Novel aromatic sulfonium compounds of general formula (I), photoacid generators comprising the same, and photopolymerizable compositions containing the same, capable of providing stereolithographic resin compositions which do not suffer from the hindrance to curing by oxygen, can easily give shaped articles having desired sizes by virtue of the high accuracy thereof in curing, and can attain a satisfactory curing depth owing to the high sensitivity thereof for radiant energy; and a stereolithographic process.

16 Claims, 2 Drawing Sheets

AROMATIC SULFONIUM COMPOUNDS, PHOTOACID GENERATORS COMPRISING THE SAME, PHOTOPOLYMERIZABLE COMPOSITIONS CONTAINING THE SAME, STEREOLITHOGRAPHIC RESIN COMPOSITIONS, AND STEREOLITHOGRAPHIC PROCESS

This application is the national phase under 35 U.S.C. § 371 of PCT International Application No. PCT/JP98/05472 which has an International filing date of Dec. 4, 1998, which designated the United States of America.

BACKGROUND OF THE INVENTION

1. Field of the Invention

The present invention relates to a novel aromatic sulfonium compound, a photoacid generator comprising the same, a photopolymerizable composition and a stereolithographic resin composition comprising the said photoacid generator, and a stereolithographic process.

2. Related Art

U.S. Pat. No. 4,058,401 discloses sulfonium compounds such as phenacyl dialkyl sulfonium, or triarylsulfonium hexafluoroantimonate, and U.S. Pat. No. 4,173,476 discloses 4-(phenylthio)phenyl diphenyl sulfonium compounds as cationic polymerization initiators, respectively. And, Japanese Patent Application Laid-open No.SHO 55-125104 and 55-125105 disclose a practical method to produce a sulfonium salt as a cationic polymerization initiator to use.

Further, Japanese Patent Application Laid-open No.HEI 7-61694, 7-25922 and 7-10914 disclose sulfonium salt having a diphenylsulfide structure with a carbonyl group at 4'-position as a cationic polymerization initiator.

Here, as for a stereolithographic process, this process is a technique, as described in Japanese Patent Application Laid-open No.SHO 60-247515, wherein a given portion of photo-curing resin placed in a vessel is exposed continuously to a beam such as argon, helium-cadmium or semiconductor laser from above to cure the exposed portion, in order to produce a desired plane of cured layer. Then the cured layer is. overlaid with another layer of the photo-curing resin, which is then photo-cured in the same manner to produce a second cured layer which continuously overlaps the first layer; and the same process is repeated to finally obtain a desired three-dimensional solid shape.

As resins previously used for the above-described stereolithographic process, mention may be made of radically polymerizing resin compositions and, for example, Japanese Patent Application Laid—open No.HEI 2-228312 and No.HEI 5-279436 disclose a stereolithographic resin composition composed mainly of (meth)acrylic resin. Further, Japanese Patent Application Laid-open No.HEI2-145616, with the aim of reducing deformation, discloses a stereolithographic resin which contains liquid resin and fine particles whose difference in apparent specific gravity is less than 0.2. For producing moldings at higher precision, a composition comprising an unsaturated ethylene-derivative monomer, a photo-initiator, and a potentially insoluble, potentially radioactive polarizing substance is reported in Japanese Patent Applications Laid-open No.HEI 3-15520, and a composition comprising an unsaturated ethylene-derivative monomer, a photo-initiator, and a potentially soluble radio-polarizing substance is reported in Japanese Patent Applications Laid-open No.HEI 3-41126. In addition, Japanese Patent Application Laid-open No.HEI 4-85314 discloses a resin composition comprising a silicone urethane acrylate, a compound having multifunctional ethylenic unsaturated bonds, and a polymerization initiator.

Besides the above-mentioned radically polymerizable resin composition, another stereolithographic resins are known cationically polymerizing resin composition. For example, Japanese Patent Application Laid-open No.HEI 1-213304 discloses an invention characterized by comprising a cationically polymerizing energy beam curable organic compound and a energy beam sensitive cationic polymerization initiator. Japanese Patent Application Laid-open No.HEI 2-28261 discloses a resin comprising a cationically polymerizing energy beam curable organic compound and a portion of a radically polymerizing radio-curing organic compound, which exhibits reduced shrinkage and improved resolution. Also, Japanese Patent Application Laid-open No.HEI 2-80423 discloses a resin composition comprising an epoxy resin, a vinyl ether resin, an energy beam sensitive cationic polymerization initiator, a radically curing resin, and an energy beam sensitive radical polymerization initiator. In addition, Japanese Patent Application Laid-open No.HEI 2-75618 discloses a stereolithographic resin composition characterized by comprising a cationically polymerizing energy beam curable organic compound, an energy beam sensitive cationic polymerization initiator, a radically polymerizing energy beam curable organic compound, an energy beam sensitive radical polymerization initiator, and a polyester having hydroxyl groups.

Further, Japanese Patent Application Laid-open No.HEI 9-87311, 9-278935 and 10-168107 disclose stereolithographic resins using a sulfonium salt having a diphenylsulfide structure with a benzoyl group at 4'-position as a photo-initiator.

However, the compound disclosed by above mentioned U.S. Pat. No. 4,058,401 can sensitize to the shortwave radiation of a mercury lamp applied usually as source of a radiation, but when the compound is used with an epoxy resin, etc., the ultraviolet ray which is necessary to activate an initiator, is intercepted owing to absorption of radiation by the resin itself and it becomes difficult to obtain a satisfactory curing performance.

In order to solve this problem, U.S. Pat. No. 4,173,476 and Japanese Patent Application Laid-open Nos. SHO 55-125104, and 55-125105 disclose the use of a sulfonium salt being able to absorb a long-wave radiation shifted, but a satisfactory curing performance is not obtained yet.

In addition, Japanese Patent Application Laid-open Nos. HEI 7-61694, 7-25922 and 7-10914 disclose sulfonium salt having a diphenylsulfide structure with a carbonyl group at 4'-position as a cationic photo-polymerization initiator, and the composition applied this compound is repported to show good storage stability, good compatibility with vinylether, good hardening and little smell of cured article, but the curing performance is insufficient.

Further, any of a radically polymerizing resin and a stereolithographic resin composition composed mainly of it is suffered from the hindrance to curing by oxygen, which results in low degree of cure on curing, so that it is necessary to carried out "post cure process" by ray or heat, which is necessarily concerned in curing of mold. In the post cure process, however, the moldings has such a disadvantage as being apt to deform. Further, these resins show large shrinkage on curing, which makes it difficult to obtain a molding with desirable dimension.

Furthermore, cationically curable stereolithographic resins as described above in Japanese Patent Application Laid-open No.HEI 1-213304, No.HEI 2-28261 and No.HEI 2-75618, have such superior characteristic properties that the post cure process are not necessary and the deformation are little, as the curing proceeds through an active group even after the beam to be exposed are shut down, and it can also easily give shaped articles having desired sizes by virtue of small shrinkage on curing. However, these resins have such disadvantages that they have insufficient sensitivity to an energy beam to be exposed, and the cured articles show insufficient mechanical properties.

And also, in the invention disclosed by Japanese Patent Application Laid-open Nos. HEI 9-87311, 9-278935 and 10-168107mentioned above, they have insufficient sensitivity to an energy beam to be exposed.

Therefore, the object of the present invention is to provide a novel compound usefull as a suitable photo-polymerization initiator being able to give a good cured article rapidly by effective absorption of the radiation from the source of a ray, photoacid generator comprising the novel compound and photopolymerizable compositions comprising the same.

And another object of the present invention is to provide a stereolithographic resin compositions, by which the above mentioned disadvantages of the prior art can be overcome, by which the prevention of curing under oxygen do not occur and a molding with desirable dimension can be obtained easily, having sufficient sensitivity to an energy beam to be exposed and to provide a stereolithographic process using the said resin composition.

SUMMARY OF THE INVENTION

The inventors have, after thorough study, succeeded to synthesize the novel aromatic sulfonium compound of the general formula (I), and have found that the said compound has good compatibilities to various resins, and is activated by effective absorption of long-wave radiation, therefore, the photo-polymerizable composition comprising the said compound can be cured rapidly to give good cured articles, and also the photo-resist comprising the same has good sensitivity and good resolution, to finally complete the present invention.

Further, the inventors have found that, when a stereolithographic resin composition comprising an aromatic sulfonium salt compound of the following general formula (I) as an energy beam sensitive cationic polymerization initiator, with a cationically polymerizing organic substance is applied to stereolithographic process by exposing to a certain specific energy beam, this resin composition do not suffer from the hindrance to curing by oxygen, can easily give shaped articles having desired sizes by virtue of the high accuracy thereof in curing, owing to the high sensitivity thereof for radiant energy, to finally complete the present invention.

That is, the present invention is an aromatic sulfonium compound expressed by a general formula (I),

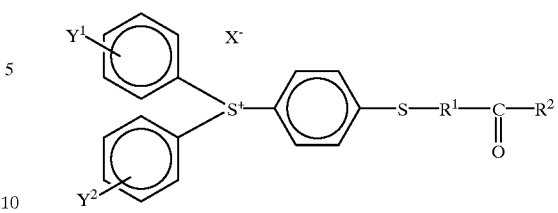

(1)

wherein, $R^1$ is a p-phenylene group, in which one or more hydrogen atoms are substituted by halogen or alkyl group, $R^2$ is a hydrocarbon radical, in which oxygen or halogen may be contained, $Y^1$ and $Y^2$ are identical or different, respectively hydrogen, halogen or oxygen, or a hydrocarbon radical, in which oxygen or halogen may be contained, X is a group of atoms, which can form a monovalent anion.

The present invention is also a photoacid generator comprising the aforementioned aromatic sulfonium compound.

Further, the present invention is a photo-polymerizable composition comprising the aforementioned photoacid generator.

Furthermore, the present invention is a stereolithographic resin composition comprising, (1) cationically polymerizing organic substance, and
(2) photoacid generator mentioned above as an energy beam sensitive catioenic polymerization initiator.

Still furthermore, the present invention is a stereolithographic process, wherein a given portion of the aforementioned stereolithographic resin composition is exposed to the beam in order to produce a desired thickness of cured layer, the energy of the beam with an emission wave length of 345 to 360 nm being not less than 70% based on the total energy of the beam with an emission wave length of 250 to 400 nm to cure the exposed portion thereof; then, the cured layer is overlaid with another layer of the stereolithographic resin composition, which is then cured in the same manner to produce a second cured layer which continuously overlaps the first layer, and the same process is repeated to finally obtain a three-dimensional molding.

In addition, the resin composition can contain, (3) radically polymerizing organic substance, and
(4) energy beam sensitive radical polymerization initiator as essential components.

The stereolithographic resin composition according to the present invention can contain an organic compound containing two or more hydroxyl groups in a molecule as an optional component.

DRAWINGS

DESCRIPTION OF THE PREFERRED EMBODIMENTS

Figure 1:
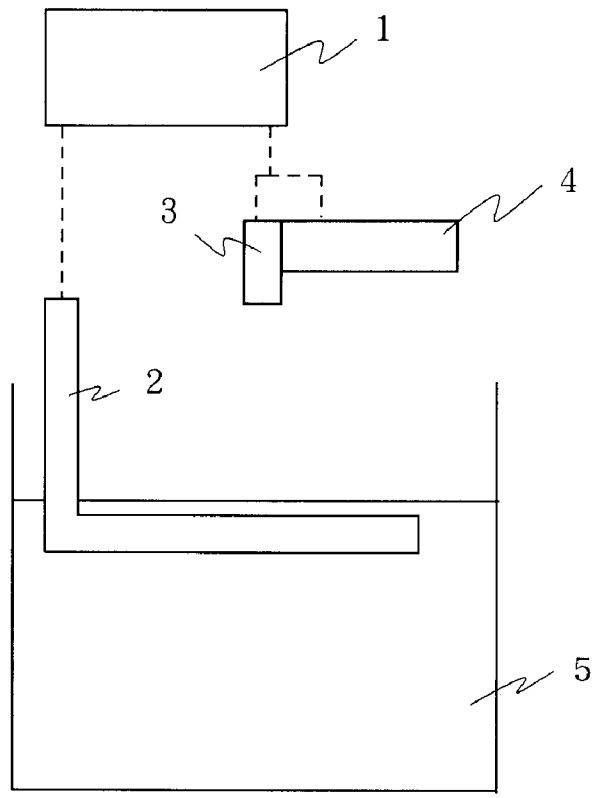
FIG. 1 is an illustration of a step to form a layer of uncured resin in the stereolithographic process.

In the general formula (I) mentioned above, $R^1$ is a p-phenylene group, in which one or more hydrogen atoms are substituted by halogen atoms or alkyl groups. For example, p-phenylene group, in which one or more hydrogen atoms are substituted by fluorine, chlorine, bromine, iodine, methyl-, ethyl-, propyl-, isopropyl-, butyl-, isobutyl-, tert-butyl-, pentyl-, isopentyl-, tert-pentyl-, neopentyl-, hexyl-, isohexyl-, heptyl-, octyl-, 2-ethylhexyl-, nonyl-, decyl-, undecyl-, dodecyl-, tridecyl-, isotridecyl-, myristyl-, palmityl-, stearyl-group and the like. The number of the such substituents are from 1 to 4, and the position of the substituents is not limited.

$R^2$ is a hydrocarbon radical, in which oxygen or halogen atom can be contained. Examples of such hydrocarbon radicals include alkyl group, halogenated alkyl group, hydroxy alkyl group, alkoxy group, phenyl group, alkylphenyl group, halogenated phenyl group, phenoxy group, hydroxy phenyl group, alkoxy carbonyl group and the like.

Examples of alkyl group mentioned above, include methyl-, ethyl-, propyl-, isopropyl-, butyl-, isobutyl-, tert-butyl-, pentyl-, isopentyl-, tert-pentyl-, neopentyl-, hexyl-, isohexyl-, heptyl-, octyl-, 2-ethylhexyl-, nonyl-, decyl-, undecyl-, dodecyl-, tridecyl-, isotridecyl-, myristyl-, palmityl-, stearyl-group and the like. And, one or more hydrogen atoms may be substituted by phenyl group or acyl group.

One of examples of halogenated alkyl group mentioned above is an alkyl group, in which one or more hydrogen atoms are substituted by halogen atoms.

Examples of alkoxy group mentioned above, include methoxy-, ethoxy-, propyloxy-, butyloxy-, pentyloxy-, hexyloxy-, heptyloxy-, octyloxy-, nonyloxy-, decyloxy-, undecyloxy-, dodecyloxy-, myristyloxy-, palmityloxy-, stearyloxy-group and the like.

In hydroxy alkyl group, halogenated alkyl group, hydroxy alkyl group and alkoxy group, the preferable carbon numbers are from 1 to 12.

In addition, when a hydrocarbon radical mentioned above has phenyl groups, one or more hydrogen atoms of the phenyl groups can be substituted by halogen atoms, alkyl group, hydroxy alkyl group, alkoxy group, hydroxyl group, ester group (alkoxycarbonyl group) and acyl group, and one or more hydrogen atoms of such a substituent can be substituted by halogen atoms, hydroxyl group etc. These alkyl group, hydroxy alkyl group, alkoxy group, hydroxyl group, ester group (alkoxycarbonyl group) and acyl group may be the same with afore mentioned group.

In the general formula (I) mentioned above, $Y^1$ and $y^2$ are identical or different, hydrogen, halogen or oxygen atom, or an alkyl group, respectively, in which can contain oxygen or halogen atoms. When $Y^1$ or $Y^2$ is an alkyl group, in which can contain oxygen or halogen atoms, the alkyl group may be the same one, described above in the case of $R^2$. The position of $Y^2$ or $Y^2$ is not limited.

In the general formula (I) mentioned above, X is a group of atoms, which can form a monovalent anion. Among the examples of $X^-$, $SbF_6^-$, $PF_6^-$, $As\ F_6^-$, $BF_4^-$, $SbCl_6^-$, $ClO_4^-$, $CF_3SO_3^-$, $CH_3SO_3^-$, $FSO_3^-$, $F_2PO_2^-$, p-toluene sulfonate, campher sulfonate, nonafluorobutane sulfonate, adamantane carboxylate, tetraaryl borate, are particularly preferable to be synthesized.

Examples of tetraaryl borate include tetraphenyl borate and its derivatives, which at least one hydrogen atom on the phenyl group is substituted by alkyl group, halogen atom, halogenated alkyl group, hydroxy alkyl group, alkoxyl group, phenyl group, alkoxycarbonyl group, and tetrakis (pentafluorophenyl)borate, tetrakis(4-fluorophenyl)borate, tetraphenyl borate.

Preferable sulfonium salts of general formula (I) mentioned above, include 4-(2-chlolo-4-benzoylphenylthio) phenyldiphenylsulfonium hexafluoroantimonate, 4-(2-chlolo-4-benzoylphenylthio)phenylbis(4-fluorophenyl)sulfonium hexafluoroantimonate, 4-(2-chlolo-4-benzoylphenylthio)phenylbis(4-chlorophenyl)sulfonium hexafluoroantimonate, 4-(2-chlolo-4-benzoylphenylthio)phenylbis(4-methylphenyl)sulfonium hexafluoroantimonate, 4-(2-chlolo-4-benzoylphenylthio)phenylbis(4-β-hydroxyethoxy)phenyl)sulfonium hexafluoroantimonate, 4-(2-methyl-4-benzoylphenylthio)phenylbis(4-fluorophenyl)sulfonium hexafluoroantimonate, 4-(3-methyl-4-benzoylphenylthio)phenylbis(4-fluorophenyl)sulfonium hexafluoroantimonate, 4-(2-fluoro-4-benzoylphenylthio)phenylbis(4-fluorophenyl)sulfonium hexafluoroantimonate, 4-(2-methyl-4-benzoylphenylthio)phenylbis(4-fluorophenyl)sulfonium hexafluoroantimonate, 4-(2,3,5,6-tetramethyl-4-benzoylphenylthio)phenylbis(4-fluorophenyl)sulfonium hexafluoroantimonate, 4-(2,6-dichloro-4-benzoylphenylthio)phenylbis(4-fluorophenyl)sulfonium hexafluoroantimonate, 4-(2,6-dimethyl-4-benzoylphenylthio)phenylbis(4-fluorophenyl)sulfonium hexafluoroantimonate, 4-(2,3-dimethyl-4-benzoylphenylthio)phenylbis(4-fluorophenyl)sulfonium hexafluoroantimonate, 4-(2-methyl-4-benzoylphenylthio)phenylbis(4-chlorophenyl)sulfonium hexafluoroantimonate, 4-(3-methyl-4-benzoylphenylthio)phenylbis(4-chlorophenyl)sulfonium hexafluoroantimonate, 4-(2-fluoro-4-benzoylphenylthio)phenylbis(4-chlorophenyl)sulfonium hexafluoroantimonate, 4-(2-methyl-4-benzoylphenylthio)phenylbis(4-chlorophenyl)sulfonium hexafluoroantimonate, 4-(2,3,5,6-tetramethyl-4-benzoylphenylthio)phenylbis(4-chlorophenyl)sulfonium hexafluoroantimonate, 4-(2,6-dichloro-4-benzoylphenylthio)phenylbis(4-chlorophenyl)sulfonium hexafluoroantimonate, 4-(2,6-dimethyl-4-benzoylphenylthio)phenylbis(4-chlorophenyl)sulfonium hexafluoroantimonate, 4-(2,3-dimethyl-4-benzoylphenylthio)phenylbis(4-chlorophenyl)sulfonium hexafluoroantimonate, 4-(2-chloro-4-acetylphenylthio)phenyldiphenyl sulfonium hexafluoroantimonate, 4-(2-chloro-4-(4-methylbenzoyl)phenylthio) phenyldiphenyl sulfonium hexafluoroantimonate, 4-(2-chloro-4-(4-fluorobenzoyl)phenylthio) phenyldiphenyl sulfonium hexafluoroantimonate, 4-(2-chloro-4-(4-methoxybenzoyl)phenylthio) phenyldiphenyl sulfonium hexafluoroantimonate, 4-(2-chloro-4-dodecanoylphenylthio)phenyldiphenyl sulfonium hexafluoroantimonate, 4-(2-chloro-4-acetylphenylthio)phenylbis(4-fluorophenyl)sulfonium hexafluoroantimonate, 4-(2-chloro-4-(4-methylbenzoyl)phenylthio)phenylbis(4-fluorophenyl)sulfonium hexafluoroantimonate, 4-(2-chloro-4-(4-fluorobenzoyl)phenylthio)phenylbis(4-fluorophenyl)sulfonium hexafluoroantimonate, 4-(2-chloro-4-(4-methoxybenzoyl)phenylthio)phenylbis (4-fluorophenyl)sulfonium hexafluoroantimonate, 4-(2-chloro-4-dodecanoylphenylthio)phenylbis(4-fluorophenyl)sulfonium hexafluoroantimonate, 4-(2-chloro-4-acetylphenylthio)phenylbis(4-chlorophenyl)sulfonium hexafluoroantimonate, 4-(2-chloro-4-(4-methylbenzoyl)phenylthio)phenylbis(4-chlorophenyl)sulfonium hexafluoroantimonate, 4-(2-chloro-4-(4-fluorobenzoyl)phenylthio)phenylbis(4-chlorophenyl)sulfonium hexafluoroantimonate, 4-(2-chloro-4-(4-methoxybenzoyl)phenylthio)phenylbis(4-chlorophenyl)sulfonium hexafluoroantimonate, 4-(2-chloro-4-dodecanoylphenylthio)phenylbis(4-chlorophenyl)sulfonium hexafluoroantimonate, 4-(2-chloro-4-benzoylphenylthio)phenyldiphenyl sulfonium hexafluorophosphate, 4-(2-chloro-4-benzoylphenylthio)phenyldiphenyl sulfonium tetrafluoroborate, 4-(2-chloro-4-benzoylphenylthio)phenyldiphenyl sulfonium perchlorate, 4-(2-chloro-4-benzoylphenylthio)phenyldiphenyl sulfonium trifluoromethanesulfonate, 4-(2-chloro-4-benzoylphenylthio)phenylbis(4-fluorophenyl)sulfonium hexafluorophosphate, 4-(2-chloro-4-benzoylphenylthio)phenylbis(4-fluorophenyl)sulfonium tetrafluoroborate, 4-(2-chloro-4-benzoylphenylthio)phenylbis(4-fluorophenyl)sulfonium perchlorate, 4-(2-chloro-4-benzoylphenylthio)phenylbis(4-fluorophenyl)sulfonium trifluoromethanesulfonate, 4-(2-chloro-4-benzoylphenylthio)phenylbis(4-fluorophenyl)sulfonium p-toluenesulfonate, 4-(2-chloro-4-benzoylphenylthio)phenylbis(4-fluorophenyl)sulfonium camphersulfonate, 4-(2-chloro-4-benzoylphenylthio)phenylbis(4-fluorophenyl)sulfonium nonafluorobutanesulfonate, 4-(2-chloro-4-benzoylphenylthio)phenylbis(4-chlorophenyl)sulfonium hexafluorophosphate, 4-(2-chloro-4-benzoylphenylthio)phenylbis(4-chlorophenyl)sulfonium tetrafluoroborate, 4-(2-chloro-4-benzoylphenylthio)phenylbis(4-chlorophenyl)sulfonium perchlorate, 4-(2-chloro-4-benzoylphenylthio)phenylbis(4-chlorophenyl)sulfonium trifluoromethanesulfonate, and the like.

Above mentioned compounds can be produced, for example, by exchange of the salts after preparing the sulfonium salts by condensation with dehydration of a substituted diphenylsulfide with a diphenyl sulfoxide in sulfuric acid.

Since the photo-acid generator of the present invention has the character to release, in situ, a Lewis acid by being exposed to an active energy beam of an ultraviolet ray, an electron beam, an X-ray, a radioactive ray, or a high-frequency wave, the photo-acid generator can initiate polymerization of a cationically polymerising organic substance. Therefore, the photo-acid generator of the present invention is useful for cationic photo-polymerization initiator.

Owing to the acyl radical in the compound of above-mentioned general formula (I), the photo-acid generator of the present invention has the sensitivity to longer wave radiation compared with the customary aromatic sulfonium salt, thus can effectively absorb the beam with an emission wave length of 365 nm, which is the brightest beam from high-pressure mercury-vapor lamp among general sources of light. Therefore, cationically polymerising composition or photo-resist, which contains the aromatic sulfonium compound of the present invention has greatly improved sensitivity, compared with cationically polymerising composition or photo-resist, which contains the previous aromatic sulfonium compound. The reactivity of the aromatic sulfonium compound of the present invention is improved, since substituents are introduced in the phenylene group, which locates between the carbonyl group in the acyl radical and sulfur atom in the sulfide structure.

(1) Cationically polymerizing organic substance, which is one component of photopolymerizable composition of the present invention is a compound which polymerizes or cross-links by cationic polymerization initiator which is activated by exposure to light.

Examples of such compounds include epoxy compounds, oxetane compounds, cyclic lactone compounds, cyclic acetal compounds, cyclic thioether compounds, spiroorthoester compounds, and vinyl compounds, which have the structure except for the cationically polymerizing organic substance. They may be used independently or in combination. Among them, epoxy compounds are suited, for their availability and ease of handling. As such epoxy compounds, aromatic, alicyclic and aliphatic epoxy resins are suited.

Further, examples of the alicyclic epoxy resins described above, include polyglycidyl ethers of poly-hydric alcohols having at least one alicyclic ring, or a compound containing cyclohexane-oxide or cyclopentene-oxide obtained by epoxidation of a compound having a structure of cyclohexene- or cyclopentene-ring with oxidant. For example, mention may be made of diglycidyl ether of hydrogenated bisphenol A, 3,4-epoxycylohexylmethyl-3,4-epoxycyclohexane carboxylate, 3,4-epoxy-1-methylcylohexyl-3,4-epoxy-1-methylhexane carboxylate, 6-methyl-3,4-epoxycylohexylmethyl-6-methyl-3,4-epoxycyclohexane carboxylate, 3,4-epoxy-3-methylcylohexylmethyl-3,4-epoxy-3-methylcyclohexane carboxylate, 3,4-epoxy-5-methylcylohexylmethyl-3,4-epoxy-5-methylcyclohexane carboxylate, 2-(3,4-epoxycyclohexyl-5,5-spiro-3,4-epoxy)cyclohexane-methadioxane, bis(3,4-epoxycyclohexylmethyl)adipate, 3,4-epoxy-6-methylcyclohexyl carboxylate, methylene bis(3,4-epoxycyclohexane), dicyclopentadiene diepoxide, ethylene bis(3,4-epoxycyclohexane carboxylate), dioctyl epoxyhexahydrophthalate, di-2-ethylhexyl epoxyhexahydrophthalate, and the like.

As the alicyclic epoxy resins described above, suitable products available commercially include UVR-6100, UVR-6105, UVR-6110, UVR-6128, UVR-6200, (from Union Carbide Co.,), Celoxide2021, Celoxide2021P, Celoxide2081, Celoxide2083, Celoxide2085, Celoxide2000, Celoxide3000, CyclomerA200, CyclomerM100, CyclomerM101, EpoleadGT-301, EpoleadGT-302, EpoleadGT-401, EpoleadGT-403, ETHB, EpoleadHD300, (from Daicel Chemical Industries, LTD.), KRM-2110, KRM-2199, (from Asahi Denka Kogyo Co. Ltd.).

Among the alicyclic epoxy resins, the epoxy resins having the structure of cyclohexene exibit preferable curing performance (fast curing).

Examples of the aromatic epoxy resins described above, include polyglycidyl ethers of polyhydric phenols having at least one aromatic ring, or their adducts with alkylene oxide, such as bisphenol A, bisphenol F, the glycidyl ethers of their adducts with alkylene oxides, or epoxy-novolac resins.

And also, examples of the aliphatic epoxy resins described above, include polyglycidyl ethers of aliphatic polyhydric alcohols or their alkylene oxide adducts, polyglycidyl esters of aliphatic, long chain, poly-basic acids, homopolymers of glycidyl acrylate or methacrylate prepared by vinyl polymerization, copolymers of glycidyl acrylate or methacrylate, prepared by vinyl polymerization with other vinyl monomer and the like. Typical examples of such compounds include glycidyl ethers of polyhydric alcohols, such as 1,4-butanediol diglycidyl ether,1,6-hexanediol diglycidyl ether, triglycidyl ether of glycerol,triglycidyl ether of trimethylol propane,tetraglycidyl ether of sorbitol, hexaglycidyl ether of dipentaerythritol, diglycidyl ether of polyethylene glycol, and diglycidyl ether of polypropylene glycol; polyglycidyl ethers of polyether-polyols, which can be obtained by adding one or more alkylene oxides with aliphatic polyhydric alcohols such as propylene glycol, trimethylol propane and glycerol; and diglycidyl esters of aliphatic, long chain di-basic acids. Further, mention may be made of mono-glycidyl ethers of aliphatic higher alcohols; mono-glycidyl ethers of phenol, cresol, butyl phenol, or polyether alcohols which can be obtained by adding alkylene oxide thereto; glycidyl esters of higher fatty acids; epoxidized soybean oil; octyl epoxy-stearate; butyl epoxystearate; epoxidized soybean oil; epoxidized polybutadiene and the like.

As the aromatic and aliphatic epoxy resins described above, suitable products available commercially include Epicoat801, Epicoat828, (from Yuka-Shell-Epoxy Co.), PY-306, 0163, DY-022, (from Ciba-Geigy Co.), KRM-2720, EP-4100, EP-4000, EP-4080, EP-4900, ED-505, ED-506, (from Asahi Denka Kogyo Co. Ltd.). Epolight M-1230, Epolight EHDG-L, Epolight 40E, Epolight 100E, Epolight 200E, Epolight 400E, Epolight 70P, Epolight 200P, Epolight 400P, Epolight 1500NP, Epolight 1600, Epolight 80MF, Epolight 100MF, Epolight 4000, Epolight 3002, Epolight FR-1500, (from Kyoeisha Chemical Co.,Ltd.), Santoto ST0000, YD-716, YH-300, PG-202, PG-207, YD-172, YDPN638, (from Tohto Kasei Co, Ltd.)

Examples of the oxetane compounds described above, include 3-ethyl-3-hydroxymethyloxetane, 3-(meta) allyloxymethyl-3- ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenylether, isobuthoxymethyl(3-ethyl-3-oxetanylmethyl)ether, isobomyloxyehtyl(3-ethyl-3-oxetanylmethyl)ether, isobomyl(3-ethyl-3-oxetanylmethyl) ether, 2-ethylhexyl(3-ethyl-3-oxetanylmethyl)ether, ethyldiethyleneglycol(3-ethyl-3-oxetanylmethyl)ether, dicyclopentadiene(3-ethyl-3-oxetanylmethyl)ether, dicyclopentenyloxyethyl(3-ethyl-3-oxetanyhnethyl)ether, dicyclopentenyl(3-ethyl-3-oxetanylmethyl)ether, tetrahydrofurfuryl(3-ethyl-3-oxetanylmethyl)ether, tetrabromophenyl(3-ethyl-3-oxetanylmethyl)ether, 2-tetrabromophenoxyethyl(3-ethyl-3-oxetanylmethyl)ether, tribromophenyl(3-ethyl-3-oxetanylmethyl)ether, 2-tribromophenoxyethyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, buthoxyethyl(3-ethyl-3-oxetanylmethyl)ether, pentachlorophenyl(3-ethyl-3-oxetanylmethyl)ether, pentabromophenyl(3-ethyl-3-oxetanylmethyl)ether, bomyl (3-ethyl-3-oxetanylmethyl)ether, 3,7-bis(3-oxetanyl)-5-oxanonane, 3,3'-(1,3, -(2-methylenyl)propanediyl bis (oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethyleneglycolbis(3-ethyl-3-oxetanylmethyl)ether, dicyclopentenylbis(3-ethyl-3-oxetanylmethyl)ether, triethyleneglycolbis(3-ethyl-3-oxetanylmethyl)ether, tetraethyleneglycolbis(3-ethyl-3-oxetanylmethyl)ether, tricyclodecanediyldimethylene(3-ethyl-3-oxetanylmethyl)ether, trimethylolpropanetris(3-ethyl-3-oxetanylmethyl)ether, 1,4-bis(3-ethyl-3-oxetanylmethoxy)butane, 1,6-bis(3-ethyl-3-oxetanylmethoxy) hexane, pentaerythritoltris(3-ethyl-3-oxetanylmethyl)ether, pentaerythritoltetrakis(3-ethyl-3-oxetanylmethyl)ether, polyethyleneglycolbis(3-ethyl-3-oxetanylmethyl)ether, dipentaerythritolhexakis(3-ethyl-3-oxetanylmethyl)ether, dipentaerythritolpentakis(3-ethyl-3-oxetanylmethyl)ether, dipentaerythritoltetrakis(3-ethyl-3-oxetanylmethyl)ether, caprolactone modified dipentaerythritolhexakis(3-ethyl-3-oxetanylmethyl)ether, caprolactone modified dipentaerythritolpentakis(3-ethyl-3-oxetanylmethyl)ether, ditrimethylolpropanetetrakis(3-ethyl-3-oxetanylmethyl)ether, ethyleneoxide modified bisphenolAbis(3-ethyl-3-oxetanylmethyl)ether, propyleneoxide modified bisphenolAbis(3-ethyl-3-oxetanylmethyl) ether, ethyleneoxide modified bisphenolA, which is reduced by hydrogen, bis(3-ethyl-3-oxetanylmethyl)ether, propyleneoxide modified bisphenolA, which is reduced by hydrogen, bis(3-ethyl-3-oxetanylmethyl)ether, ethyleneoxide modified bisphenolF(3-ethyl-3-oxetanylmethyl)ether, and the like. These compounds may be used independently or in combination. These oxetane derivatives may be used preferably to effect flexible property for the molding.

The cationically polymerizing organic substances, which are described above as components of photo-polymerizable composition, can be applied as well as (1) cationically polymerizing organic substances used in the stereolithografic resin composition of the present invention.

Furthermore, it is particularly preferable to employ an epoxy compound having cyclohexen oxide structure in a molecule among the epoxy compounds described above in an amount of 30 or more % by weight based on catinically polymerizing organic substances to effect good curing performance (curing rate) and moldings at high precision, as the stereolithographic resin composition. As 70% or.less by weight of the cationically polymerizing organic substances, use may be made of epoxy compound except for the one mentioned above or a cationically polymerizing organic substance except for epoxy compounds, as listed below. And also, it is preferable to employ the mixture of the catinically polymerizing organic substances except for epoxy compounds and the cyclohexen oxide compound mentioned above.

Examples of cationically polymerizing organic substances except for epoxy compounds, which can be employ in this invention, include oxetane compounds described above; oxorane compounds such as tetrahydrofuran and 2,3-dimethyl-tetrahydrofuran; cyclic acetal compounds such as trioxane, 1,3-dioxorane and 1,3,6-trioxan-cyclooctane; cyclic lactones such as β-propiolactone and ε-caprolactone; thiirane compounds such as ethylene sulfide and thioepichlorohydrine; thietane co cationically polymerizing organic substances, use may be made of the cationically compounds such as 1,3-propine sulfide and 3,3-dimethyl thietane; cyclic thio-ether compounds such as tetrahydrothiophene derivatives;vinyl ether compounds such as ethylene glycol divinylether, alkyl vinylether, 2-chloroethyl vinylether, 2-hydroxyethyl vinylether, triethyleneglycol divinyl ether, 1,4-cyclohexane dimethanol divinyl ether, hydroxybuthyl vynil ether, propenyl ether of propyleneglycol; ethylenic unsaturated compounds such as spiro-ortho ester compounds obtained by the reaction of epoxy compounds with lactones, styrene, vinyl cyclohexene, isobutylene and polybutadiene, and the derivatives thereof.

In the stereolithographic resin composition, it is preferable to employ the oxetane compound as the cationically polymerizing organic substance in an amount of 30% or more by weight based on total cationically polymerizing organic substances to effect flexible property for the molding. As the remaining 70% or.less by weight of the polymerizing organic substances except for the oxetane compounds mentioned above such as epoxy resins.

As (1) cationically polymerizing organic substances, the cationically polymerizing organic substances described above can be used independently or in combination.

As photopolymerization initiator, a photo-acid generator can be used without limitation in the customary range of use, however, a photo-acid generator is preferably used at the content of 0.05 to 10 parts by weight based on the 100 parts by weight of a cationically polymerizing organic substance. But, according to the performance of a cationically polymerizing organic substance, the intensity of the beam to be exposed, period to be cured and the cost facter, it can be used out of range described above.

The radically polymerizable photo-polymerizing composition such as acrylic resin and unsaturated polyester can be used mixing with the photo-polymerizable composition of the present invention.

If desired, a photosensitizer, such as anthracene derivative or pyrene derivative thermosensitive cationic polymerization initiator, filler, diluent, solvent, pigment, flexibilizer, defoarner, leveling agent, thickener, stabilizer, flame retardant, antioxidant, may be added in the stereolithographic resin composition of the present invention.

The photo-polymerizing composition of the present invention is useful for wide application, for example manufacturing of printing plate for litho printing or relief printing, photo-resist for manufacturing of printed board, IC and LSI, image processing such as relief image and printed image copy, photo-curable ink, coating or adhesives etc.

In the stereolithographic resin, afore-mentioned (2) energy beam sensitive cationic polymerization initiator can be used preferably at the content of 0.05 to 10% by weight, more preferably at the content of 0.1 to 10% based on the (1) cationically polymerizing organic substance. When the content exceeds this range, the cured articles have insufficient strength, and in the case of below the cure of the resin is insufficient.

(3) Radically polymerizing organic substance, which is used according to the present invention, is a radically polymerizing organic substance which polymerizes or crosslinks upon exposure to an energy beam in the presence of a energy beam sensitive radical polymerization initiator and, preferably, has at least one unsaturated double bond per one molecule.

Examples of such compounds include acrylate compounds, methacrylate compounds, allyl urethane compounds, unsaturated polyester compounds, and styrene series compounds.

Among these radically polymerizing organic substances, those having (meth)acrylic groups, such as epoxy (meth)acrylates, urethane (meth)acrylates, polyester (meth)acrylates, polyether (meth)acrylates, (meth)acrylic esters of alcohols, are best suited, for their availability and ease of synthesis and handling.

Here, epoxy (meth)acrylates refer to acrylates which are obtained by the reaction of, for example, a known aromatic, alicyclic or aliphatic epoxy resin and (meth)acrylic acid. The most preferable of these epoxy (meth)acrylates are the (meth)acrylates of aromatic epoxy resins which are obtained by the reaction of a polyglycidyl ether of a polyhydric phenol having at least one aromatic nuclei or an added alkylene oxide thereof, and (meth)acrylic acid. One example is the (meth)acrylate obtained by the reaction of a glycidyl ether and (meth)acrylic acid, the former obtained by the reaction of bisphenol A or an added alkylene oxide thereof and epichlorohydrin. Another example is the (meth)acrylate obtained by the reaction of an epoxy novolac resin and (meth)acrylic acid.

The most preferable urethane (meth)acrylates are those obtained by the reaction of one or more polyesters or polyethers having a hydroxyl group, a (meth)acrylic ester having a hydroxyl group, and an isocyanate, and those obtained by the reaction of a (meth)acrylic ester having a hydroxyl group and an isocyanate.

Among polyesters having a hydroxyl group, the most preferable ones are those obtained by the reaction of one or more aliphatic polyhydric alcohols and one or more polybasic acids. Examples of the aliphatic polyhydric alcohols include 1,3-butanediol, 1,4-butanediol, 1,6-hexanediol, diethylene glycol, triethylene glycol, neopentyl glycol, polyethylene glycol, polypropylene glycol, polybutylene glycol, trimethylolpropane, glycerol, pentaerythritol, and dipentaerythritol. Examples of the polybasic acids include adipic acid, terephthalic acid, phthalic anhydride, and trimellitic acid.

Among polyethers having a hydroxyl group, the most preferable ones are those obtained by adding one or more alkylene oxides to a aliphatic polyhydric alcohol. Examples of the aliphatic polyhydric alcohols are such as those listed above. Examples of the alkylene oxides include ethylene oxide and propylene oxide.

Among (meth)acrylic esters having a hydroxyl group, the most preferable ones are those obtained by the esterification of an aliphatic polyhydric alcohol and (meth)acrylic acid. Examples of the aliphatic polyhydric alcohols are such as those listed above.

The best suited of these (meth)acrylic esters having a hydroxyl group are those obtained by the esterification of a aliphatic dihydric alcohol and (meth)acrylic acid, such as 2-hydroxyethyl (meth)acrylate.

Among isocyanates, the most preferable ones are those having one or more isocyanic group per one molecule, particularly divalent isocyanic compounds such as tolylene diisocyanate, hexamethylene diisocyanate, and isophorone diisocyanate.

The most preferable polyester (meth)acrylates are those obtained by the reaction of a polyester having a hydroxyl group and (meth)acrylic acid. Among polyesters having a hydroxyl group, the most preferable ones are those obtained by the esterification of one or more aliphatic polyhydric alcohols and one or more monoacids, polybasic acids and phenols. Examples of the aliphatic polyhydric alcohols are such as those listed above. Examples of the monoacids include formic acid, acetic acid, butyl carbonic acid, and benzoic acid. Examples of the polybasic acids include adipic acid, terephthalic acid, phthalic anhydride, and trimellitic acid. Examples of the phenols include phenol, p-nonyl phenol, bisphenol A, and the like. The most preferable polyether (meth)acrylates are those obtained by the reaction of a polyether having a hydroxyl group and (meth)acrylic acid. Among polyethers having a hydroxyl group, the most preferable ones are those obtained by adding one or more alkylene oxides to an aliphatic polyhydric alcohol. Examples of the aliphatic polyhydric alcohols are such as those listed above. Examples of the alkylene oxides include ethylene oxide, propylene oxide and the like.

The most preferable (meth)acrylic esters of alcohols are (meth)acrylates obtained by the reaction of an aromatic or aliphatic alcohol having at least one hydroxyl group per one molecule or an added alkylene oxide thereof, and (meth) acrylic acid. Examples of such (meth)acrylates include 2-ethylhexyl (meth)acrylate, 2-hydroxyethyl (meth)acrylate, 2-hydroxypropyl (meth)acrylate, isoamyl (meth)acrylate, lauryl (meth)acrylate, stearyl (meth)acrylate, isooctyl (meth) acrylate, tetrahydrofurfuryl (meth)acrylate, isobonyl (meth) acrylate, benzyl (meth)acrylate, 1,3-butanediol di(meth) acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth) acrylate, polyethylene glycol di(meth)acrylates, polypropylene glycol di(meth)acrylates, trimethylolpropane tri(meth) acrylate, pentaerythritol tetra (meth)acrylate, dipentaerythritol hexa(meth)acrylate, and ε-caprolactone-modified dipentaerythritol hexa(meth)acrylate.

Among these (meth)acrylate, poly(meth)acrylate of polyhydric alcohols are particularly preferable.

As the radically polymerizing organic substance described above, suitable products available commercially, for example of monovalent products, include AronixM-101, M-102, M-111, M-113, M-117, M-152, TO-1210(from Toagosei Co., Ltd.), Kayarad TC-110S, R-564, R-128H, (from Nippon Kayaku Co., Ltd.), Biscoat192, Biscoat220, Biscoat2311HP, Biscoat2000, Biscoat2100, Biscoat2150, Biscoat8F, Biscoatl7F, (from Osaka Yuki Chemical Ind.,).

And, for example of polyvalent products, include SA1002, (from Mitsubishi Chemical Co., Ltd.,), Biscoatl95, Biscoat230, Biscoat260, Biscoat215, Biscoat310, Biscoat214HP, Biscoat295, Biscoat300, Biscoat360, BiscoatGPT, Biscoat400, Biscoat700, Biscoat540, Biscoat3000, Biscoat3700, (from Osaka Yuki Chemical Ind.,), Kayarad FR-526, HDDA, NPGDA, TPGDA, MANDA, R-551, R-712, R-604, R-684, PET-30, GPO-303, TMPTA, THE-330, DPHA, DPHA-2H, DPHA-2C, DPHA-21, D-310, D-330, DPCA-20, DPCA-30, DPCA-60, DPCA-120, DN-0075, DN-2475, T-1420, T-2020, T-2040, TPA-320, TPA-330, RP-1040, RP-2040, R-011, R-300, R-205, (from Nippon Kayaku Co.,Ltd.), AronixM-210, M-220, M-233, M-240, M-215, M-305, M-309, M-310, M-315, M-325, M-400, M-6200, M-6400, (from Toa Gosei Co., Ltd.), Light AcrylateBP-4EA, BP-4PA, BP-2EA, BP-2PA, DCP-A, (from Kyoeisha Chemical Co.,Ltd.), NewfrontierBPE-4, TEICA, BR-42M, GX-8345, (from Dai-Ichi Kogyo Seiyaku Co.,Ltd.), ASF-400, (from Nippon Steel Chemical Co.,Ltd.) Ripoxy SP-1506, SP-1507, SP-1509, VR-77, SP-4010, SP-4060, (from Showa Highpolymer Co., Ltd.), NK EsterA-BPE-4, (from Shin-Nakamura Chemical Co.,Ltd.).

The above radically polymerizing organic substances may be used independently or in combination to attain a desired property.

It is also preferable that 50% by weight or more based on the radically polymerizing organic substance is a compound having (meth)acrylic group in the molecule.

The content of the radically polymerizing organic substance used in the present invention is preferably not more than 200 parts by weight, particularly preferably 10 to 100 parts by weight, based on 100 parts by weight of the cationically polymerizing organic substances.

The (4) energy beam sensitive radical polymerization initiator, used in the present invention, is a compound, which enables to initiate the radical polymerization upon exposure to an energy beam, and preferably includes ketone series compounds such as acetophenone series compounds, benzyl series compounds and thioxanthone series compounds.

Acetophenone series compounds include, for example, diethoxyacetophenone, 2-hydroxy-2-methyl-1-phenylpropane-1-one, 4'-iso-propyl-2-hydroxy-2-methylpropiophenone, 2-hydroxymethyl-2-methylpropiophenone, 2,2-dimethoxy-1,2-diphenylethane-1-one, p-dimethylaminoacetophenone, p-tert-butyldichloroacetophenone, p-tert-butyltrichloroacetophenone, p-azidobenzalacetophenon, 1-hydroxycyclohexylphenylketone, 2-methyl-1-[4-(methylthio)phenyl]-2-morpholinopropanone-1, 2-benzyl-2-dimethylamino-1-(4-morpholinophenyl)-butanone-1, benzoin, benzoin methyl ether, benzoin ethyl ether, benzoin isopropyl ether, benzoin-n-butyl ether, benzoin isobutyl ether 1-[4-(2-hydroxyethoxy)phenyl]-2-hydroxy-2-methyl-1-propane-1-on, and the like.

Benzyl series compounds include benzyl, anisyl and the like.

Benzophenone series compounds include, for example, benzophenone,methyl o-benzoyl benzoate, Michier's ketone, 4,4'-bisdiethylamino benzophenone, 4,4'-dichlorobenzophenone, 4-benzoyl-4'-methyldiphenyl sulfide and the like.

Thioxanthone series compounds include thioxanthone, 2-methylthioxanthone, 2-ethylthioxanthone, 2-chlorothioxanthone, 2-isopropylthioxanthone, 2,4-diethylthioxanthone and the like.

Other energy beam sensitive radical polymerization initiators include 2,4,6-trimethylbenzoyldiphenyl phosphine oxide, bis(cyclopentadienyl)-bis[2,6-difluoro-3-(pyl-1-yl)] titanium and the like.

The above energy beam sensitive radical polymerization initiators may be used independently or in combination to attain a desired property.

The content of (4) energy beam sensitive radical polymerization initiator described above can be stoichiometric quantity, and it is preferably 0.05 to 10% by weight, more preferably 0.1 to 10% by weight, based on the weight of (3) radically polymerizing organic substances. When the content exceeds this range, the cured articles have insufficient strength, and in the case of below the cure of the resin is insufficient.

The curing rate of the resin composition containing (4) energy beam sensitive radical polymerization initiator, mixed with (3) radically polymerizing organic substance, exhibits much improved in the stereolithographic process, compared with the other composition, thus such composition is preferable for stereolithographic resin composition.

(5)Organic compounds having two or more hydroxyl groups per one molecule and (6)thermoplastic polymers, may be added in the stereolithographic resin composition according to the present invention as optional components.

Preferable examples of above-mentioned (5)organic compounds having two or more hydroxyl groups per one molecule, include polyhydric alcohols, polyethers containing hydroxy groups, polyesters containing hydroxy groups and polyhydric phenols.

Examples of the polyhydric alcohols include ethylene glycol, propylene glycol,neopentyl glycol, trimethylolpropane, glycerol, pentaerythritol, dipentaerythritol, 1,3-butanediol, 1,4-butanediol, 1,6-hexanediol, 1,4-cyclohexane dimethanol, 4,8-bis (hydroxymethyl)tricyclo[5,2,1,0$^{2.6}$,]decane, and the like.

The polyether containing hydroxy groups means a compound obtained by adding one or more alkylene oxide to one or more polyhydric alcohols or one or more polyhydric phenols. Examples of the polyhydric alcohols and polyhydric phenols used therein include ethylene glycol, propylene glycol, neopentyl glycol, trimethylolpropane, glycerol, pentaerythritol, dipentaerythritol, 1,3-butanediol, 1,4-butanediol, 1,6-hexanediol, bisphenol A, bisphenol F, phenol novolak, cresol novolak and the like. On the other hands, examples of the alkylene oxides include propylene oxide, ethylene oxide and the like.

Further, examples of the polyester containing hydroxy groups include a polyester obtained by esterificatioin of one or more polyhydric alcohols and/or polyhydric phenols with one or more monobasic or polybasic acids, and a polyester obtained by esterification of one or more lactones with one or more polyhydric alcohols. Examples of the polyhydric alcohols or polyhydric phenols such as those listed above. Examples of the monobasic acids include formic acid, acetic acid, butyl carbonic acid, benzoic acid and the like. Examples of the polybasic acids include adipic acid, terephthalic acid, trimellitic acid and the like. Examples of the lactones include β-propiolactone, and ε-caprolactone.

The polyhydric phenol means a compound containing two or more hydroxy groups, bonded directly to aromatic ring, per one molecule, such as bisphenol A, bisphenol F, phenol novolak resin and cresol novolak resin listed above.

The above-mentioned (5)organic compounds having two or more hydroxyl groups per one molecule may be used independently or in combination to attain a desired property.

The content of the organic compound having two or more hydroxy groups per one molecule is preferably 1 to 50 parts by weight based on the 100 parts by weight of (1) cationically polymerizing organic substances in the resin composition.

(6)The thermoplastic polymer compound is a polymer compound which is in a liquid or solid state at room temperature and can be uniformly mixed with the resin composition at room temperature.

Typical examples of such thermoplastic polymer compounds include polyester, polyvinyl acetate, polyvinyl chloride, polybutadiene, polycarbonate, polystyrene, polyvinyl ether, polyvinylbutyral, polyacrylate, polymethyl methacrylate, polybutene, and styrene-butadiene block copolymer hydrogenated.

Derivatives of these thermoplastic polymer compounds having functional groups such as a hydroxyl, carboxyl, vinyl or epoxy group may also be used.

The preferable number-average molecular weight of said thermoplastic polymer compound as used in the present invention is 1000 to 500000, more preferably 5000 to 100000. A molecular weight outside this range may be practicable; however, an excessively low molecular weight would fall to attain desired improvement in strength, and excessively high one would increase the viscosity of the resin composition, making it unsuited for optical solid molding.

And, the content of said thermoplastic polymer compound, is 5 to 50% preferablly 5 to 30% by weight. When the content is less than low limit, no effect is observed. In the case of higher content than higher limit, the composition becomes disadvantagous as a stereolithographic resin composition because the viscosity of the composition becomes too high.

The resin composition according to the present invention with the thermoplastic polymer compound further improves the mechanical properties of the cured resin in the stereolithograpphic process, compared with the same composition without it, and as a result, the resulting composition is preferable stereolithograpphic resin composition.

If desired, a photosensitizer, which is not essential, may be added in the stereolithograpphic resin composition of the present invention. For example, the combination of the photo-sensitizer such as anthracene derivative or pyrene derivative further improves the cure rate compared with the resin composition without the photo-sensitizer, and as a result, more preferable resin composition can be obtained.

Various resin additives, such as thermosensitive cationic polymerization initiator, inorganic filler, organic filler, coloring agent such as pigment or dye, leveling agent, defoamer, thickener, flame retardant, antioxidant and stabilizer may be added as desired in the amounts of their normal use, provided that they do not impair the advantage of the present invention. As the thermosensitive cationic polymerization initiater, for example, onium salts described in Japanese Patent Application Laid-open No.SHO 57-49613 and SHO 58-37004, can be mentioned.

Various resin additives, such as thermosensitive cationic polymerization initiator, inorganic filler, organic filler, coloring agent such as pigment or dye, leveling agent, defoamer, thickener, flame retardant, antioxidant and stabilizer may be added as desired in the amounts of their normal use, provided that they do not impair the advantage of the present invention. However, it is preferable that are limited to 150% by weight or below based on the total amount of the stereolithographic resin composition of the present invention, so as not to amplify the distortion of the obtained molding.

In the present invention, the beam, to which the afore-mentioned stereolithographic resin composition is exposed, is preferably the ultraviolet laser. The example of the beam include helium-cadmium laser, argon ion laser and neodymium-oscilatory laser with an emission wave length converted to one third by combination with non-linear crystal. Also, the beam, in which the energy of the beam with an emission wave length of 345 to 360 nm is more than 70%, based on the total energy of the beam with an emission wave length of 250 to 400 nm, is more preferable.

In that case the beam with an emission wave length of less than 250 nm, or more than 400 nm, is not useful to cure the afore-mentioned stereolithographic resin composition, that is not useful to activate the energy beam sensitive cationic polymerization initiator. However, they may be used, if desired.

Thus, the total energy of the beam with an emission wave length of 250 to 400 nm must be more than the required energy enough to cure the afore-mentioned stereolithographic resin composition, that is enough to activate the energy beam sensitive cationic polymerization initiator.

If the energy of the beam with an emission wave length of 345 to 360 nm is not more than 70%, based on the total energy of the beam with an emission wave length of 250 to 400 nm, the beam cannot be absorbed enough to cure, so that the depth to be cured for the resin becomes too deep, and the needless cured portion is made owing to cure the needless portion.

Examples of the beam, in which the energy of the beam with an emission wave length of 345 to 360 nm is more than 70%, based on the total energy of the beam with an emission wave length of 250 to 400 nm include Nd solid type laser(e.g. Nd-YVO4 laser, Nd-YAG laser) with an emission wave length converted to one third (355 nm) by combination with non-linear crystal, and the laser beam with an emission wave length of 351nm rich made by treatment through filter from argon ion laser(333 nm, 351 nm and 364 nm).

The first step to carry out the stereolithographic process according to the present invention is to prepare a stereolithographic resin composition from afore-mentioned essential constituents for the stereolithographic resin composition, optional constituents if desired and the other materials.

This preparing process may be performed in a known manner by, for example, thoroughly mixing the components by blade turbine agitation, roll kneading, or other method. The preferred compounding ratio of (1) through (4) described above, and the types and contents of the additives to be mixed as necessary may be selected according to the aforementioned stereolithographic resin composition of the present invention. Thus obtained stereolithographic resin composition is generally in a liquid state at room temperature.

In the next step, a given portion of the stereolithographic resin composition is exposed to an energy beam to cure the exposed portion thereof, in order to produce a desired thickness of cured layer; then, the cured layer is overlaid with another layer of the energy beam curing resin composition, which is radio-cured in the same manner to produce a cured layer which continuously overlaps the first above-described cured; and the same process is repeated to finally obtain a three-dimensional solid shape.

Figure 2:
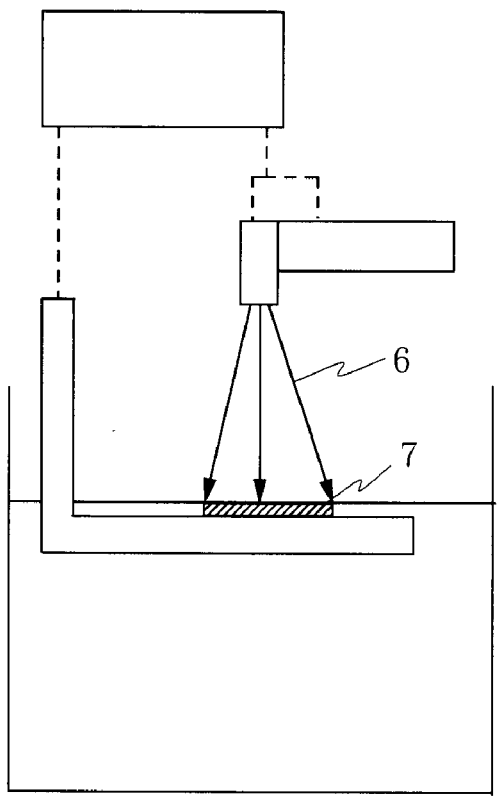
FIG. 2 is an illustration of a step to form a first cured layer in the stereolithographic process.
Figure 3:
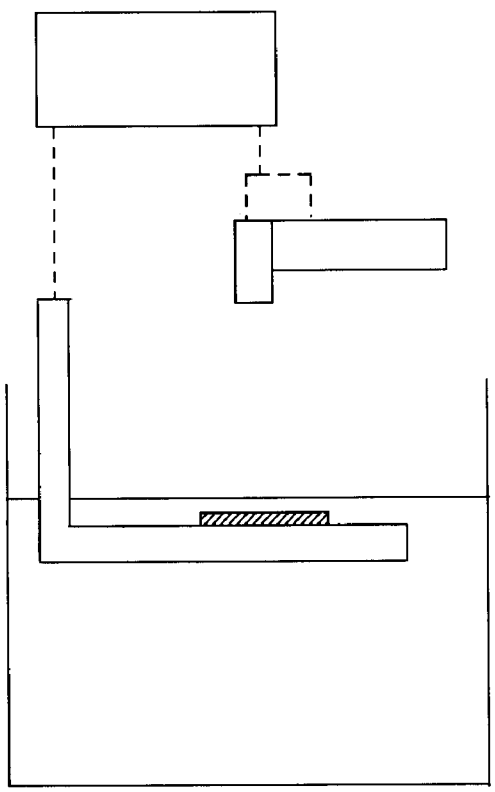
FIG. 3 is an illustration of a step to form a second layer of uncured resin on the first cured layer in the stereolithographic process.
Figure 4:
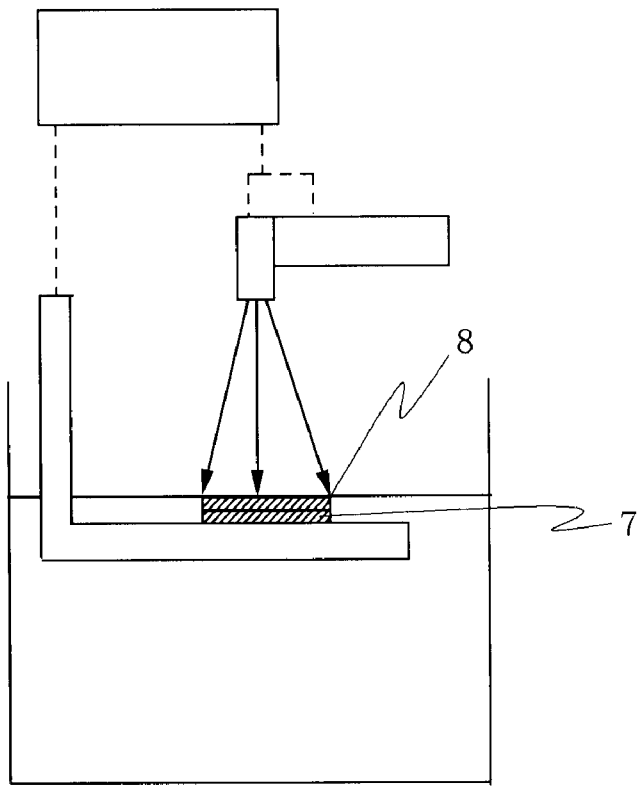
FIG. 4 is an illustration of a step to form a second cured layer in the stereolithographic process.

Furthermore, the process mentioned above is shown according to FIG. 1 through FIG. 4. In FIG. 1 the NC table 2 is set in the resin 5, then the layer of uncured resin is formed with a certain depth, which corresponds to the thickness of the layer of uncured resin. Next, by a signal from control section 1 according to CAD data, the surface of the uncured resin is exposed to scanning radiation by the laser beam 6 from laser source 4 to obtain the first cured layer 7 (cf. FIG. 2). By a signal from control section 1, in turn, the NC table 2 is moved down to form the second layer of uncured resin with the certain thickness on the first cured layer. (cf. FIG. 3). the uncured resin is exposed to scanning radiation by the laser beam 6 in the same manner to obtain the second cured layer 8. (cf. FIG. 4). The same process is repeated to finally obtain the molding.

The following examples and comparative examples are given for the purpose of illustration for the embodiment of this invention.

SYNTHESIS EXAMPLE (1)

Synthesis of 4-(2-chloro-4-benzoylphenylthio) phenylbis(4-fluorophenyl)sulfonium Hexafluoroantimonate. (Compound I: the following formula)

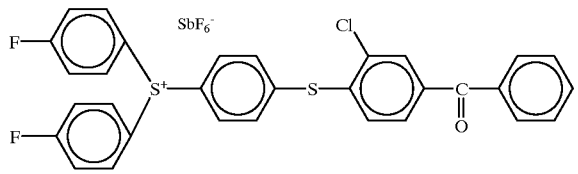

Synthesis was carried out via three steps, as follows:
(1) Synthesis of 3,4-dichloro Benzophenone.

70.3 g of benzoyl chloride was added into the mixture of aluminium chloride (93.3 g) and 1,2-dichloro benzene (14.7 g) using 500 mL three necked flask, then reaction was carried out for 12 hrs. at 120° C. The reaction mixture was poured into 1000 g of ice water in a beaker (5000 mL), and further, 1000 g of toluene was added. The toluene layer was washed by 1000 g of water three times. After condensing the toluene layer under reduced pressure, 87 g of 3,4-dichlorobenzophenone was obtained (yield 69%)
(2) Synthesis of 3-chloro4-phenylthio-benzophenone.

150 g of dimethyl formamide, 27.5 g of benzenethiol and 20.0 g of natrium hydroxide were mixed in 500mL three necked flask, and the mixture was heated at 100° C. With stirring the mixture, four alliquots of 3,4-dichloeobenzophenone (total 62.8 g)were poured into the mixture sequentially, and stirring was continued for 3 hrs. After cooling of the reaction mixture, 500 g of toluene were added, and the toluene layer was washed by 500 g of water five times. Condensing the toluene layer under reduced pressure, 76 g of 3-chloro-4-phenylthio-benzophenone were obtained (yield 94%).
(3) Synthesis of 4-(2-chloro-4-benzoylphenylthio)phenylbis(4-fluorophenyl)sulfonium Hexafluoroantimonate.

47.7 g of 4,4'-difluorodiphenyl sulfide were added into 300 g of sulfuric acid with stirring using 1000 mL three necked flask. After 4,4'-difluorodiphenyl sulfide was dissolved clearly, five alliquots of 3-chloro-4-phenylthio-benzophenone (total 65.0 g) were added sequentially. As soon as adding, the reaction mixture was colored to dark gray. Stirring was continued for 24 hrs. at room temperature. Then, the reaction mixture and 300 g of toluene were poured into 500 g of methanol and 500 g ice in 3000mL beaker. The underlayer was separated out, and after it was neutralised with 40% aqueous natrium hydrixide solution, 1500 g of ethyl acetate was added therein, and stirring was continued.

66 g of KSbF6 was added therein, and stirring was continued for two hours. After the ethyl acetate layer was washed with 1000 g of water twice, 139 g of 4-(2-chloro-4-benzoylphenylthio)phenylbis(4-fluorophenyl)sulfonium hexafluoro-antimonate was obtained as white powder (yield 89%) by condensing under reduced pressure.

The results of analysis are shown as follows;

| Infrared absorption spectrum( ketone) Elementary analysis | ν (C=O) calcd | 1760 cm$^{-1}$ found |
| --- | --- | --- |
| C | 47.7% | 48.5% |
| H | 2.6% | 3.2% |
| S | 8.2% | 8.5% |
| Sb | 15.6% | 13.8% |
| Cl | 4.5% | 6.5% |

Identification of chemical structure was carried out by $^1$H-NMR and $^{13}$C-NMR.

SYNTHESIS EXAMPLE (2)

Synthesis of 4-(2-chloro-4-benzoylphenylthio) phenylbis(4-fluorophenyl)sulfonium Hexafluorophosphate. (Compound II: the following formula)

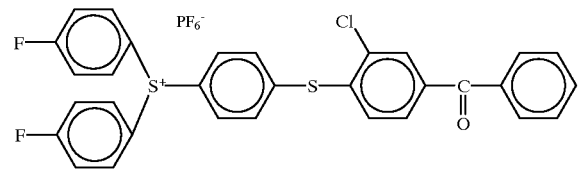

In the same manner as in Synthesis example (1), KPF$_6$ was used instead of KSbF$_6$. And the Compound II was obtained as white powder. Identification was carried out by Infrared absorption spectrum, elementary analysis, $^1$H-NMR and $^{13}$C-NMR.

SYNTHESIS EXAMPLE (3)

Synthesis of 4-(2-chloro4-benzoylphenylthio) phenyldiphenyl Sulfonium Hexafluoro-antimonate. (Compound III: the following formula)

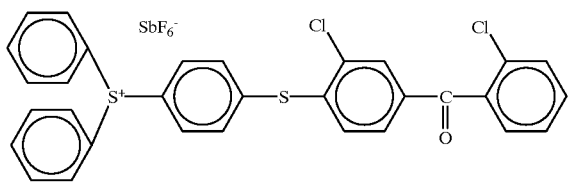

In the same manner as in Synthesis example (1), diphenylsulfide was used instead of 4,4'-difuluorodiphenylsulfide and the Compound III was obtained as white powder.

Identification was carried out by Infrared absorption spectrum, elementary analysis, $^1$H-NMR and $^{13}$C-NMR.

SYNTHESIS EXAMPLE (4)

Synthesis of 4-(2-chloro-4-benzoylphenylthio) phenyldiphenyl Sulfonium Hexafluoro-phosphate (Compound IV: the following formula)

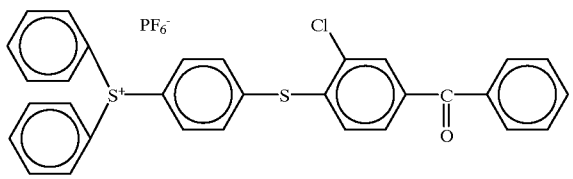

In the same manner as in Synthesis example (3), KPF$_6$ was used instead of KSbF$_6$ and the Compound IV was obtained as white powder. Identification was carried out by Infrared absorption spectrum, elementary analysis, $^1$H-NMR and $^{13}$C-NMR.

SYNTHESIS EXAMPLE (5)

Synthesis of 4-(2-chloro-4-benzoylphenylthio) phenylbis(4-hydroxyethoxyphenyl)sulfonium Hexafluoro-antimonate. (Compound V : the following formula)

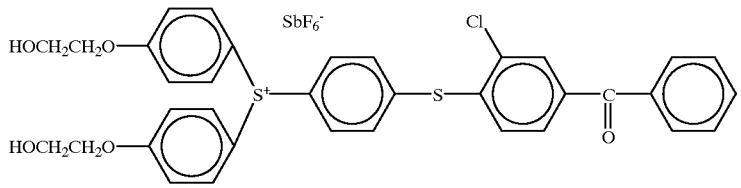

In the same manner as in Synthesis example (1), 4,4'-bishydroxyethoxyphenylsulfide was used instead of 4,4'-difuluorodiphenylsulfide and the Compound V was obtained as white powder. Identification was carried out by Infrared absorption spectrum, elementary analysis, $^1$H-NMR and $^{13}$C-NMR.

SYNTHESIS EXAMPLE (6)

Synthesis of 4-(2-chloro-4-benzoylphenylthio) phenylbis(4-hydroxyethoxyphenyl)sulfonium Hexafluoro-phosphate(Compound VI: the following formula)

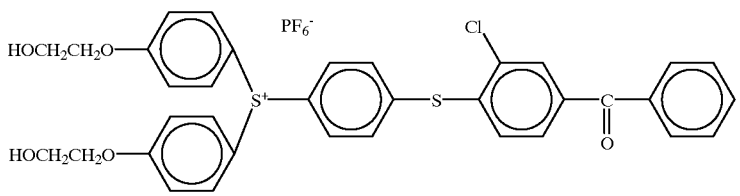

In the same manner as in Synthesis example (5), KPF$_6$was used instead of KSbF$_6$ and the Compound IV was obtained as white powder. Identification was carried out by Infrared absorption spectrum, elementary analysis, $^1$H-NMR and $^{13}$C-NMR. The following compounds were also tested for comparative test.
(Compound VII: the following formula)

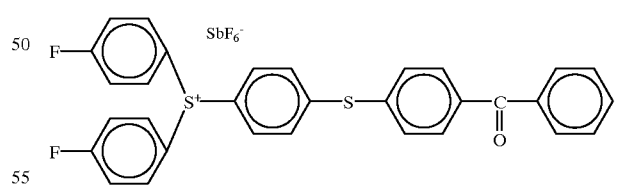

(Compound VIII: the following formula)

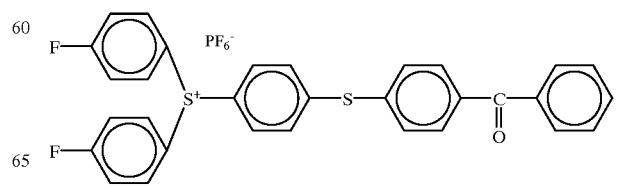

Test 1

Spectral exposure test, The photo-curable resin composition containing the photo-acid generator, which consists of aromatic sulphonium salt, mentioned above were prepared. The quantity of photo-acid based on 100 g of 3,4-epoxy cyclohexylmethyl-3,4-epoxy cyclohexyl carboxylate are shown in following Table 1. The photo-curable resin composition was coated on a glass plate with bar-coater(No. 6), which was 10 μm thick. The spectral sensitivity of the photo-curable resin composition exposed to an emission wave-length of 365 nm, applying spectrometer CT-25CP from Jasco Corporation.

This spectrometer is provided with built-in high-pressure mercury-vapor lamp and diffraction grating, thus monochromatic light of an emission wave length of 365 nm can be radiate and the radiation energy can be controlled by regulation of the exposing time with the shutter. A movable stage, on which the glass plate coated by the above mentioned photo-polymerizable composition can be set, is provided right below the shutter. The stage can be work in connection with the shutter, and the photo-polymerizable composition can be exposed to thirteen different levels of energy. After exposure, the glass plate, coated with photo-polymerizable composition was developed by methanol. The minimum energy to cure by an emission wave length of 365 nm was determined by the number of the remaining cured film, the luminous energy of an emission wave length of 365 nm and the period of exposure. The test results were shown in Table 1.

TABLE 1

| Compound | Quantity (mmol) | Sensitivity (energy required to cure) (365 nm) (mJ/cm$^2$) |
| --- | --- | --- |
| I | 1.0 | 22 |
| II | 4.0 | 22 |
| III | 1.0 | 22 |
| IV | 4.0 | 22 |
| V | 1.0 | 22 |
| VI | 4.0 | 22 |
| VII | 1.0 | 39 |
| VIII | 4.0 | 39 |

In Table 1, it is clear that the novel sulfonium salts (I to VI) of the present invention have more improved sensitivity to long wave radiation with an emission wave length of 365 nm, compared with previously known sulfonium salts (VII, VIII).

Test 2

Afore mentioned compounds I to VI were added as photo initiators to the mixture of 80 g of 3,4-epoxy cyclohexylmethyl-3,4-epoxy cyclohexane carboxylate with 20 g of 1,4-butane diol diglycidyl ether at the content as shown in Table 1, and the mixture was blended enough uniformly. The mixture was coated on an aluminium coated paper with bar-coator(No. 3). This sample composition was exposed to radiation from 80 W/cm high-pressure mercury-vapor lamp by the specrometer provided with beltconveyar. The distance between lamp and beltconveyar was 10 cm and line speed of the beltconveyar was 5 cm/min.

After curing, the sample was held at room temperature for 24 hrs. Then the surface of the sample was tested by return rubbing 200 times with an applicator soaked by MEK (methyl ethyl ketone). As any resin composition was suffered by no damage even after 200 times return rubbing, it was found that the curing was carried out sufficiently and the cured article has good solvent resistance.

Test 3

Afore mentioned compounds I to VI were added as photo initiators to the mixture of 80 g of 3,4-epoxy cyclohexylmethyl-3,4-epoxy cyclohexane carboxylate with 20 g of 1,4-butane diol diglycidyl ether at the content as shown in Table 1, and the mixture was blended enough uniformly. The mixture was coated on a polyethylene terephthalate film 50 μm thick with bar-coater(No. 3). This sample composition was exposed to radiation from 80 W/cm high-pressure mercury-vaor lamp by the spectrometer provided with beltconveyor. The distance between lamp and beltconveyar was 10 cm and line speed of the beltconveyor was 5 cm/min.

After curing, the sample was held at room temperature for 24 hrs. Then the pencil hardness of the cured sample was determined by a pencil hardness-tester under 1 kg of load. Every result determined was 2 H hardness.

Now, with regard to the stereolithographic resin composition and the stereolithographic process, the examples and the comparative examples are setting forth according to the present invention. In the examples and the comparative examples, the term "parts" means "parts by weight".

EXPERIMENT 1

The Precision of the Molding (the length and the width) and the Molding Test

The stereolithographic resin composition was tested in the stereolithographic experimental system which consisted of a movable NC table, an optical system(together with a laser system) and a control computer, and the box, which is filled with the molding and have the dimension of 100 mm length, 100 mm width and 10 mm height, was obtained from the above resin composition by curing it in steps of 0.1 mm thickness according to CAD data. The differences between the cured article and CAD data about the length and the width, were determined. Also, the properties and the appearance of the model were observed.

EXPERIMENT 2

The Determination of the Sensitivity

Using the same system as the Experiment 1, the sensitivity of the resin was tested according to the procedure described in ("Kohsoku sanjigen seikei no kiso" (that is, the basement of the rapid, three dimensional molding), editted and author by Paul F. Jacobs, p. 258, 1993, published by Nikkei Publishing Center.).

EXPERIMENT 3

The Precision of the Molding (the thickness of the needless cured portion to the depth)

Using the same system as the Experiment 1, a specimen having the shape shown in FIG. 1, was obtained. There is no support under the portion near the center of the specimen. Provided that the absorption of the beam is insufficient, when the resin portion near the center is curing, the needless cured portion is formed. As curing of the needless cured portion is insufficient, this portion is softer compared with the normal cured portion. The thickness of the needless cured portion was determined by being scraped out with a knife.

EXPERIMENT 4

The measurement of the Mechanical Strength

Using the same system as the Experiment 1, a bending test specimen and an impact test specimen were obtained. The specimen were tested for bending strength, Izod impact strength (notched) and elongation in tension according to the test method described in JIS-6911.

The materials used for the Examples and Comparative examples were as follows:

For (1) the cationically polymerizing organic substances (hereafter "cationic resins"), cationic resins 1 to 5 as shown below were used:

Cationic resin 1: 3,4-epoxycyclohexylmethyl-3,4-epoxycyclohexane carboxylate.

Cationic resin 2: 1,4-butanedioldiglycidyl ether.

Cationic resin 3: bis(3,4-epoxycyclohexylmethyl) adipate.

Cationic resin 4: bisphenolA diglycidil ether.

Cationic resin 5: 1,4-bis[(3-ethyl-3-oxetanylmethoxy) methyl]benzene.

For (2) the energy beam sensitive cationic polymerization initiators (hereafter "cationic initiators"), cationic initiators 1 to 5 as shown below were used:

Cationic initiator 1: 4-(2-chlolo-4-benzoylphenylthio) phenyldiphenylsulfonium hexafluoroantimonate.

Cationic initiator 2: 4-(2-chlolo-4-benzoylphenylthio) phenylbis(4-fluorophenyl) sulfonium hexafluoroantimonate.

Cationic initiator 3: 4-(4-benzoylphenylthio) phenylbisdiphenylsulphonium hexafluoroantimonate.

Cationic initiator 4: 4,4'-bis(diphenylsulfonio) phenylsulfide-bis-hexafluruolo antimonate.

Cationic initiator 5: 4,4'-bis[bis(β-hydroxyethoxy) phenyl]sulphonio phenylsulfide-bis-hexafuluoro antimonate.

For (3) the radically polymerizing organic substances (hereafter "radical resins"), radical resins 1 to 3 as shown below were used:

Radical resin 1: dipentaerythritol hexaacrylate.

Radical resin 1: acrylate of bisphenolA epoxide.

Radical resin 1: trimethylolpropane triacrylate.

For (4) the energy beam sensitive radical polymerization initiators (hereafter "radical initiators"), radical initiators 1 and 2 as shown below were used:

Radical initiator 1: 2-hydroxy-2-methyl-1-phenylpropane-1-on.

Radical initiator 2: 1-[4-(2-hydroxyethoxy)phenyl]-2-hydroxy-2-methyl-1-propane- 1-on.

Following three kind of laser were applied in the Experiments.

Nd-YV04: Nd-YV04 laser having an emission wave length converted by combination with non-linear crystal. Wave length 355 nm, Pulse-oscilatory laser (from Spectra Physics Co., Trade name: BLIO-355Q).

Ar-1 : Ultraviolet-oscilatory argon ion laser. Mixed wave length of 333, 351 and 364 nm (from Coherent, Inc. Trade name : INNOVA325. Rate of energy of an emission wave length of 351 nm is 44%).

Ar-2: Ultraviolet-oscilatory argon ion laser. Mixed wave length of 351 nm(main) and 333 nm(minor) (from Coherent, Inc. Trade name: INNOVA325/0165-148-00. Rate of energy of an emission wave length of 351 nm is 76%).

EXAMPLE 1

A resin composition mixed at the content as shown in Table 2, was blended enough to obtain the stereolithographic resin composition. The resin composition was a pale yellow, transparent liquid. Using the resin composition, Experiment 1 to 4 was tested by employing the laser shown in Table 2. The test result was shown in Table 2.

EXAMPLE 2 to 8 and COMPARATIVE EXAMPLE 1 to 3

In the same manner, Example 2 to 8 and Comparative example 1 to 3. The test result was shown in Table 2 to 4.

TABLE 2

| | Example | | | | | |
|---|---|---|---|---|---|---|
| | 1 | 2 | 3 | 4 | 5 | 6 |
| Cationic resin 1 | 75 | 75 | 55 | 55 | 55 | 35 |
| Cationic resin 2 | 25 | 25 | 15 | 15 | 15 | 20 |
| Cationic resin 3 | — | — | — | — | — | 15 |
| Cationic resin 4 | — | — | — | — | — | 20 |
| Cationic initiator 1 | 2 | — | 2 | 2 | 2 | — |
| Cationic initiator 2 | — | 2 | — | — | — | 2 |
| Cationic initiator 3 | — | — | — | — | — | — |
| Cationic initiator 4 | — | — | — | — | — | — |
| Cationic initiator 5 | — | — | — | — | — | — |
| Radical resin 1 | — | — | 20 | 20 | 20 | 5 |
| Radical resin 2 | — | — | — | — | — | 5 |
| Radical resin 3 | — | — | 10 | 10 | 10 | — |
| Radical initiator 1 | — | — | 0.5 | 0.5 | 0.5 | — |
| Radical initiator 2 | — | — | — | — | — | 0.5 |
| Type of laser | Ar-1 | Ar-1 | Ar-1 | Ar-2 | Nd-YVO4 | Ar-1 |
| Bending strength (kg/cm²) | 600 | 510 | 720 | 610 | 730 | 810 |
| Izod (kg · cm/cm²) | 5.1 | 5.2 | 6.1 | 5.3 | 5.9 | 6.9 |
| Precision of moldings (length and breadth) (mm) | 0.011 | 0.012 | 0.010 | 0.015 | 0.014 | 0.011 |
| Sensitivity (mJ/cm²) | 9.8 | 9.9 | 8.3 | 9.0 | 7.6 | 8.1 |
| Precision of moldings (Needless cured portion) (mm) | 0.16 | 0.14 | 0.15 | 0.05 | 0.04 | 0.15 |

TABLE 3

| | Example | |
|---|---|---|
| | 7 | 8 |
| Cationic resin 1 | — | 40 |
| Cationic resin 5 | 100 | 50 |
| Cationic initiator 1 | 2 | 2 |
| Radical resin 1 | — | 10 |
| Radical initiator 1 | — | 0.5 |
| Type of laser | Nd—YVO4 | Nd—YVO4 |
| Bending strength (kg/cm²) | 600 | 710 |

TABLE 3-continued

|  | Example 7 | Example 8 |
|---|---|---|
| Izod (kg · cm/cm$^2$) | 9.0 | 7.5 |
| Precision of moldings (length and breadth) (mm) | 0.009 | 0.010 |
| Sensitivity (mJ/cm$^2$) | 6.9 | 8.0 |
| Precision of moldings (Needless cured portion) (mm) | 0.05 | 0.04 |
| Elongation in tension (%) | 10 | 14 |

TABLE 4

|  | Comparative example 1 | Comparative example 2 | Comparative example 3 |
|---|---|---|---|
| Cationic resin 1 | 55 | 55 | 55 |
| Cationic resin 2 | 15 | 15 | 15 |
| Cationic resin 3 | — | — | — |
| Cationic resin 4 | — | — | — |
| Cationic initiator 1 | — | — | — |
| Cationic initiator 2 | — | — | — |
| Cationic initiator 3 | 2 | — | — |
| Cationic initiator 4 | — | 2 | — |
| Cationic initiator 5 | — | — | 2 |
| Radical resin 1 | 20 | 20 | 20 |
| Radical resin 2 | — | — | — |
| Radical resin 3 | 10 | 10 | 10 |
| Radical initiator 1 | 0.5 | 0.5 | 0.5 |
| Radical initiator 2 | — | — | — |
| Type of laser | Ar-1 | Ar-1 | Ar-1 |
| Bending strength (kg/cm$^2$) | 550 | 380 | 400 |
| Izod (kg · cm/cm$^2$) | 4.9 | 3.9 | 3.8 |
| Precision of moldings (length and breadth) (mm) | 0.013 | 0.015 | 0.020 |
| Sensitivity (mJ/cm$^2$) | 17.1 | 27.5 | 29.4 |
| Precision of moldings (Needless cured portion) (mm) | 0.15 | 0.24 | 0.23 |

Industrial Feasibility

It appears that the aromatic sulfonium compound of the present invention can be activated by effective absorption of long-wave radiation, and can act as a suitable photo-acid generator. Therefore, since the photo-polymerizable resin composition, which contains the photo-acid generator, can be cured rapidly to give a good cured article, which has improved properties, a photoresist made of this photo-polymerizable resin composition has good sensitivity and good resolution. By employing the stereolithographic resin compositions, which comprizes the aromatic sulfonium compound of the present invention, disadvantages of the prior art can be overcome, this resin composition do not suffer from the hindrance to curing by oxygen, can easily give shaped articles having desired sizes by virtue of the high accuracy thereof in curing, owing to the high sensitivity thereof for radiant energy and can be cured with formation of only a little needless cured portion and without formation of ply separation. Thus, the stereolithographic process employing afore-mentioned resin composition have been provided.

What is claimed is:

1. An aromatic sulfonium compound expressed by a general formula (I),

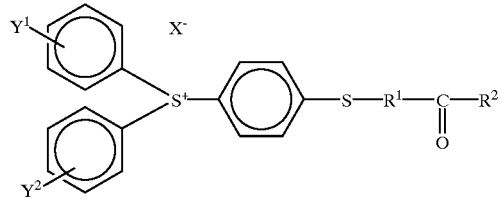

(1)

wherein, $R^1$ is a p-phenylene group, in which one or more hydrogen atoms are substituted by halogen or alkyl group, $R^2$ is a hydrocarbon radical, in which oxygen or halogen may be contained, $Y^1$ and $Y^2$ are identical or different, respectively hydrogen, halogen or oxygen, or a hydrocarbon radical, in which oxygen or halogen may be contained, X is a group of atoms, which can form a monovalent anion.

2. An aromatic sulfonium compound of claim 1, wherein $R^2$ is,
   a) an alkyl group, in which one or more hydrogen may be substituted by a group selected from the group consisting of halogen, phenyl, alkoxy, phenoxy, acyl and ester group, or
   b) phenyl group, in which one or more hydrogen may be substituted by a group selected from the group consisting of hydroxyl group, halogen, phenyl, alkoxy, phenoxy, acyl and ester group.

3. An aromatic sulfonium compound of claim 1 or 2, wherein $Y^1$ and $Y^2$ are identical or different, respectively, and each is any group selected from the group consisting of hydrogen, halogen, alkyl, alkoxy, acyl, polyoxyalkylene and ester group.

4. An aromatic sulfonium compound of claim 1, wherein $X^-$ is an anion selected from the group consisting of $SBF_6^-$, $PF_6^-$, $AsF_6^-$, $BF_4^-$, $SbCl_6^-$, $ClO_4^-$, $CF_3SO_3^-$, $CH_3SO_3^-$, $FSO_3^-$, $F_2PO_2^-$, sulfonate, campher sulfonate, nonafluorobutane sulfonate, adamantane carboxylate and tetraaryl borate.

5. A photo-acid generator comprising the aromatic sulfonium compounds of claim 1.

6. A photo-polymerizable composition comprising the photo-acid generator of claim 5 and one or more of (1) cationically polymerizing organic substances.

7. A photo-polymerizable composition of claim 6, wherein at least one substance among the afore-mentioned one or more of (1) cationically polymerizing organic substances is an organic compound having one or more epoxy group in a molecule.

8. A stereolithographic resin composition comprising (1) cationically polymerizing organic substances and the photo-acid generator of claim 5 as (2) energy beam sensitive cationic polymerization initiator, as essential components.

9. A stereolithographic resin composition of claim 8, which additionally comprises (3) radically polymerizing organic substance and (4) energy beam sensitive radical polymerization initiator, as the essential components.

10. A stereolithographic resin composition of claim 8 or 9, which comprises a compound having the cyclohexeneoxide structure in a molecule at the content of 30% or more by weight based on (1) cationically polymerizing organic substances.

11. A stereolithographic resin composition of claim 8 or 9, wherein the cationically polymerizing organic substances comprise a compound having an oxetane structure at the content of 30% or more by weight based on (1) cationically polymerizing organic substances.

12. A stereolithographic resin composition of claim 9, wherein the radically polymerizing organic substances comprise a compound having (meth)acrylic groups at the content of 50% or more by weight based on (3) radically polymerizing organic substance.

13. A stereolithographic process, wherein a given portion of an energy beam curing resin composition is exposed to an energy beam to cure the exposed portion thereof, in order to produce a desired thickness of cured layer; then, the cured layer is overlaid with another layer of the energy beam curing resin composition, which is radio-cured in the same manner to produce a cured layer which continuously overlaps the first above-described cured layer; and the same process is repeated to finally obtain a three-dimensional molding; which comprises using the stereolithographic resin composition of claim 8.

14. A stereolithographic process of claim 13, wherein the energy beam is an ultraviolet ray.

15. A stereolithographic process of claim 13, wherein the stereolithographic resin composition is exposed to the beam, the energy of the beam with an emission wave length of 345 to 360 nm being not less than 70%, based on the total energy of the beam with an emission wave length of 250 to 400 nm.

16. A stereolithographic process of claim 13 or 14, wherein the energy beam is a laser beam.

* * * * *